US006280510B1

(12) United States Patent
Kelderman et al.

(10) Patent No.: US 6,280,510 B1
(45) Date of Patent: Aug. 28, 2001

(54) INK COMPOSITION FOR A MELTABLE INK

(75) Inventors: Erik Kelderman, Venlo; Roelof Hendrik Everhardus, Lomm; Nicolina M. Kortenhoeven, Venlo, all of (NL)

(73) Assignee: Oce-Technologeis B.V., Venlo (NL)

( * ) Notice: Subject to any disclaimer, the term of this patent is extended or adjusted under 35 U.S.C. 154(b) by 0 days.

(21) Appl. No.: 09/360,146

(22) Filed: Jul. 26, 1999

(30) Foreign Application Priority Data

Aug. 3, 1998 (NL) .................................................. 1009791

(51) Int. Cl.[7] .................................................. C09D 11/00
(52) U.S. Cl. ..................................... 106/31.29; 106/31.61
(58) Field of Search .............................. 106/31.29, 31.61

(56) References Cited

U.S. PATENT DOCUMENTS 4,931,095 6/1990 Nowak et al. .................... 106/31.29
5,122,187 6/1992 Schwarz et al. .................. 106/31.29
5,185,035 * 2/1993 Brown et al. ..................... 106/31.29
5,421,868 6/1995 Ayalia-Esquilin et al. ....... 106/31.29
5,876,492 * 3/1999 Malhotra et al. ................. 106/31.58
5,958,119 * 9/1999 Malhotra et al. ................. 106/31.43
6,071,986 * 6/2000 Everhardus et al. ................. 523/160

FOREIGN PATENT DOCUMENTS 9110711 7/1991 (WO) .

OTHER PUBLICATIONS

Ricoh Co Ltd., 06 200202, Jul. 19, 1994 (Abstract).
Dorogov, M.V., vol. 126, No. 14, 1997, Chemical Abstracts, no month available.

* cited by examiner

*Primary Examiner*—Helene Klemanski
*Assistant Examiner*—Veronica F. Faison

(57) ABSTRACT

An ink composition for a meltable ink usable in a printing apparatus in which ink droplets are ejected from ink ducts, the ink composition containing an amorphously solidifying monomer compound, which compound shows a crystallinity of less than 1% when a melt of the compound is cooled at a rate of 5° C./min to past its solidification path and is then heated at a rate of 20° C./min to above its melting temperature. The monomer compound can be used in a binder for the ink composition. When inks of this kind are transferred to a receiving material, it results in greater stability in the printed layers, with respect to gum, scratch, fold resistance and transparency.

14 Claims, 2 Drawing Sheets

INK COMPOSITION FOR A MELTABLE INK

BACKGROUND OF THE INVENTION

The present invention relates to an ink composition for a meltable ink usable in a printing apparatus in which ink droplets are ejected from ink ducts. The present invention also relates to an ink composition for a meltable ink usable in a printing apparatus, said composition containing a meltable base material. The present invention also relates to a number of esters derived from 2,2'-biphenol.

Ink compositions are well known, for example, from U.S. Pat. No. 5,122,187. However, such ink compositions generally result in printed ink layers which are either too brittle or too soft on the receiving materials, so that the gum, scratch and fold resistance (GKV), particularly of the different ink layers of different colors disposed on one another is inferior.

In order to toughen ink formulations which are too brittle or to stiffen crystalline materials which are too soft, it is necessary to use an amorphous binder. After the cooling of the melting ink composition the printed images are then less vulnerable. The amorphous state also ensures good light transmission, this being favorable for color fastness and use on overhead sheets.

It is known from U.S. Pat. No. 5,421,868 that these amorphous binders can considerably increase the viscosity of the ink in the melted state, this being a disadvantage with respect to the operation of the printing apparatus. For this reason it is preferred to use binders which contain monomer compounds.

It is well known that monomer compounds, e.g. waxes, are generally crystallizable. The purer the compound and the lower the molecular weight, the easier it is to form a crystal lattice. However, binders are known which contain monomer compounds, which, when used in an ink composition for a printing apparatus, solidify amorphously on the receiving material. If an ink provided with such binders is printed on a receiving material, said binders admittedly form an amorphously solidified phase, but in the course of time they will exhibit partial after-crystallization. The result is that the properties of the printed layer change so that the gum, scratch and fold resistance decreases, the color impression changes and the transparency is reduced.

SUMMARY OF THE INVENTION

It has been surprisingly been found that if binders are used which contain esters of 2,2'-biphenol and acids with an aromatic character, no after-crystallization occurs in the printed ink layer under normal ambient conditions, despite the low molecular weight of these esters. As a result of avoiding after-crystallization, the binder according to the present invention is particularly suitable for use as a carrier material for an ink composition, in which the binder is the main constituent of the ink composition. These inks yield printed layers which retain their good properties for very long periods when they are stored under normal conditions. A good ink composition can also be obtained with a binder according to the present invention in which the ink also contains a meltable base material in the form of a crystalline-solidifying monomer compound and an amorphous polymer or oligomer binder. By a careful choice of the constituents, these inks can be adjusted very well with respect to melting behavior in the printing apparatus and penetration behavior in the receiving material.

It has been found that good stability of a printed layer is combined with the absence of "cold crystallization" (a phenomenon in which crystallizable substances present in a solid amorphous state crystallize under the influence of the supply of heat) of a monomer compound according to the present invention, under the following conditions: cooling of the melted compound at the very low rate of 5° C./min to past the solidification point and then heating the solidified compound at a rate of 20° C./min to past the melting temperature. More suitable are those compounds which themselves remain completely amorphous when the melt is cooled at 5° C./min to past its solidification point and then heated from the solidified state at the even lower rate of 5° C./min to past the melting temperature. Particularly suitable compounds are those which also remain amorphous when blended with the oligomer binder Crystalbond 509 of Printlas™ (compound: Crystalbond=2:1 weight/weight), and stored for 48 hours at 50° C. Ink compositions provided with such compounds yield printed layers which ever after some months' storage under normal conditions show no deterioration in GKV and transparency.

The binders known heretofore always have partial crystallization under these conditions. However, esters of 2,2'-biphenol and methoxybenzoic acid or methylbenzoic acid do not exhibit crystallization under any of the conditions described above, and are also new compounds.

BRIEF DESCRIPTION OF THE DRAWINGS

The present invention will now be explained by reference to the following examples and Figures, wherein.

DETAILED DESCRIPTION OF THE INVENTION

Example 1

Thermal Analysis of Monomer Compounds

Figure 1:
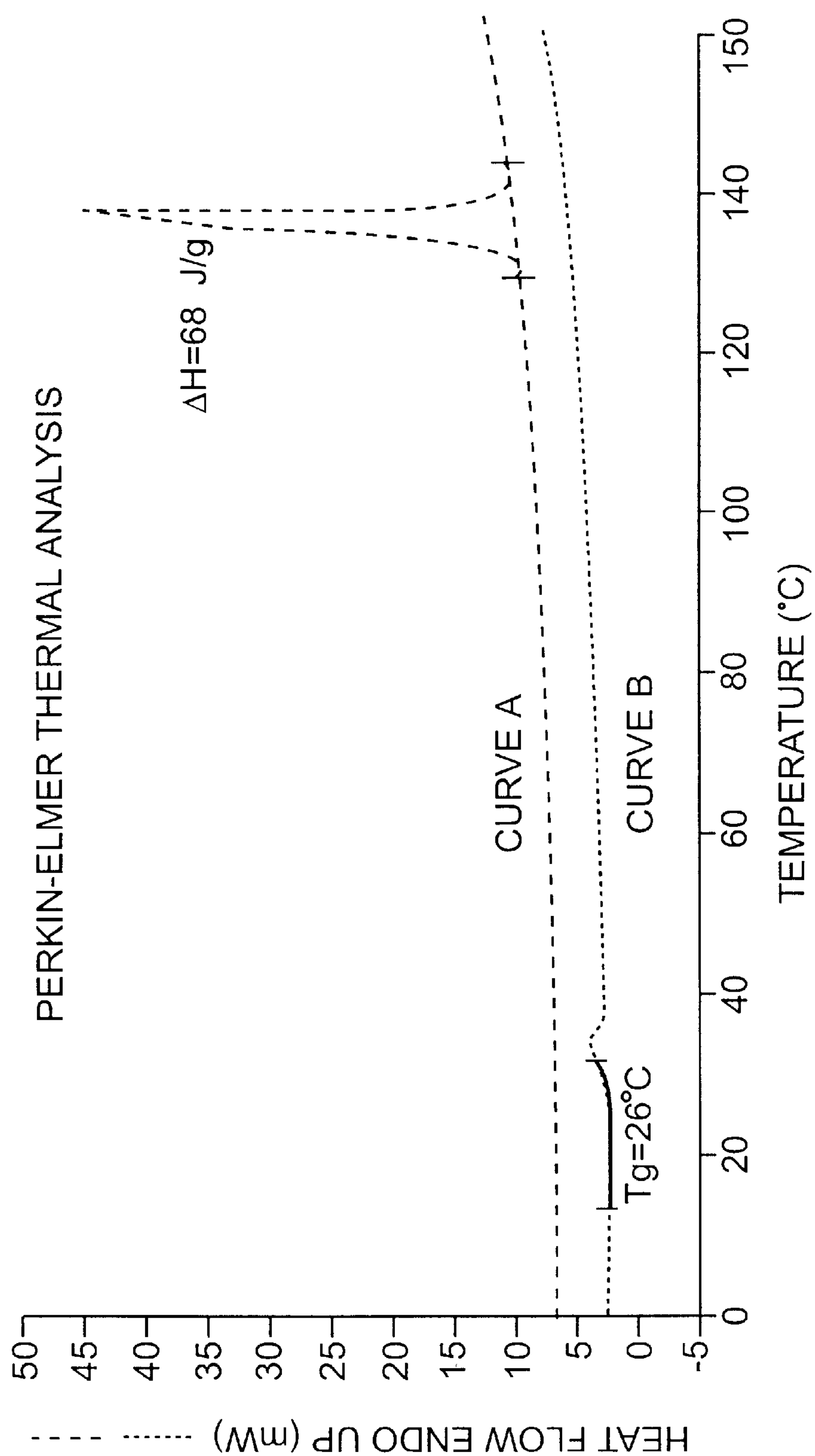
FIG. 1 is a thermogram of a compound according to the present invention and FIG. 2 is a thermogram of an amorphously solidifying monomer compound having undesirable after-crystallization.

FIG. 1 is a graph showing the relationship of the melting and solidification behavior (a thermogram), expressed in quantities of absorbed energy to the temperature, plotted with a Differential Scanning Calorimeter (DSC), of a binder according to the present invention. An example of a DSC measuring instrument is the Perkin Elmer DSC-7, of Perkin Elmer Co., Norwalk, Conn.; and FIG. 2 is a graph showing the relationship of the melting and solidification behavior, expressed in quantities of absorbed energy to the temperature, plotted with the same Differential Scanning Calorimeter, of a binder which under normal conditions exhibits undesirable after-crystallization.

Figure 2:
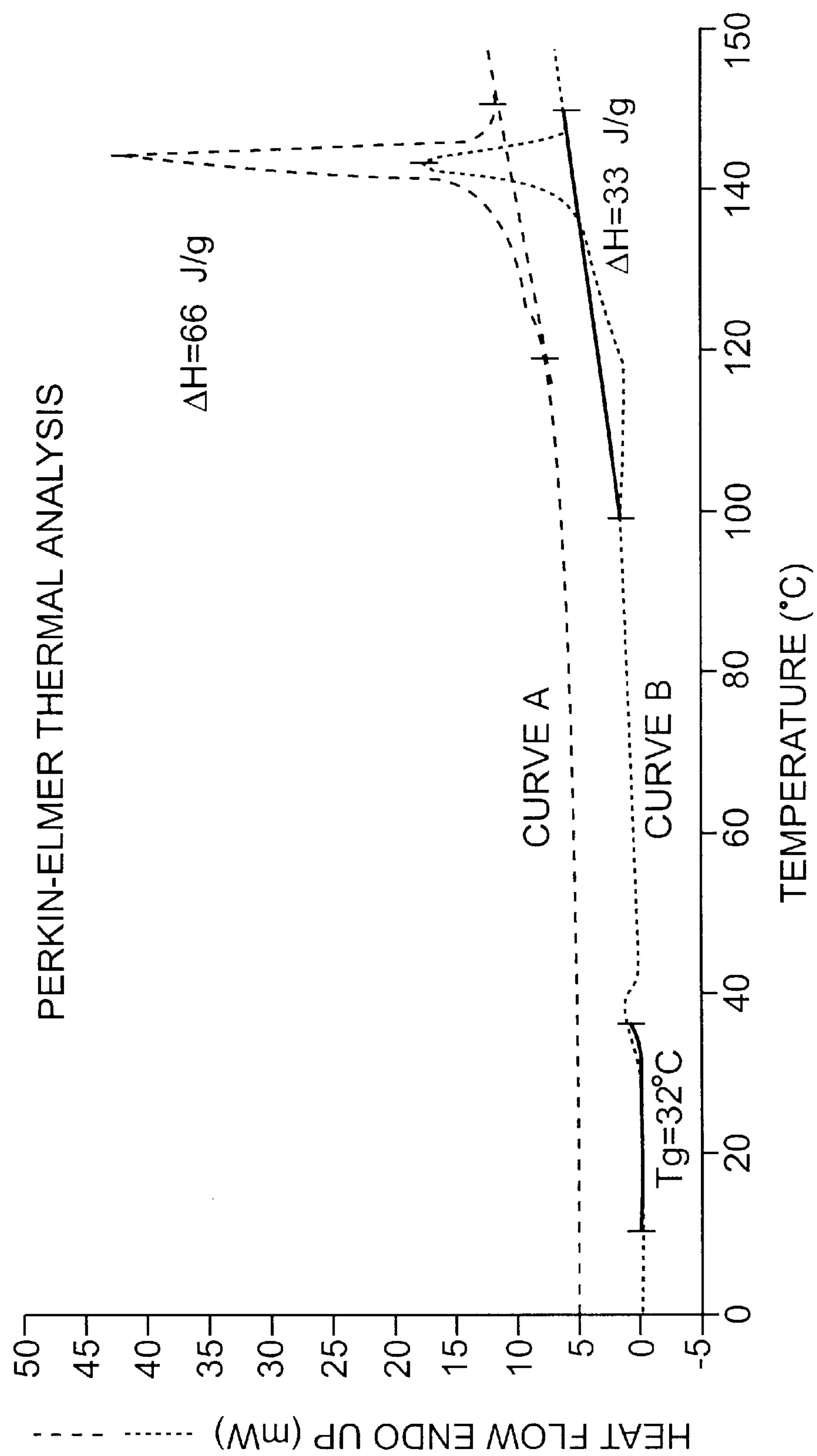

The favorable property of the binder according to the present invention can best be understood from the thermograms of the pure compounds as shown in FIGS. 1 and 2. The thermograms are plotted starting with the compounds in their crystalline phase as obtained by recrystallization from ethanol.

FIG. 1 is the thermogram of BIPANI (see Table 1). When this compound is heated from a temperature of 0° C. at a rate of 20° C./min (curve A), it melts at a temperature of about 125° C. The accompanying melting heat is 68 J/g. When the melt is cooled at a rate of 5° C./min to past its solidification path (in the case of BIPANI this path is around a temperature of 30° C.), the compound passes from a liquid phase to a solid phase, known as glass transition. If the compound is then re-heated at a rate of 20° C./min (curve B, for the sake of clarity 5 mW shifted on the y-axis with respect to curve A), to above the previously determined melting temperature, only the glass transition at 26° C. is observed. Thus under these conditions the compound is no longer able to crystallize. Technically this is referred to as the absence of (cold) crystallization.

FIG. 2 is a comparable thermogram of another amorphously solidifying monomer compound which under normal conditions does exhibit undesirable after-crystallization, namely an ester of dipentaerythritol (di-PETPC). This compound melts at about 136° C. After cooling of the melt with the above cooling rate, this compound passes into a solid phase at a temperature of about 32° C. On the subsequent heating at a rate of 20° C./min the compound starts to crystallize at a temperature of about 95° C., this being visible in the curve by the formation of a negative peak which extends to 132° C. There is therefore cold crystallization. On further heating, the compound starts to melt again. It will be apparent from the thermogram that under these conditions the compound has partially crystallized because the melting heat no longer reaches the initial level: 33 Jg with respect to the original 66 Jg. By dividing these values, the crystallinity value of the compound under these conditions can be established to be 50% in the case of di-PETPC.

It is apparent from the figures that the amorphous state of a compound according to the present invention is more stable than that of a compound which after-crystallizes when it is transferred in an ink composition to a support material. Table 1 shows, in addition to a number of compounds according to the present invention, a number of other amorphously solidifying monomer compounds. The Table also indicates which compounds when used in a binder for an ink composition exhibit undesirable after-crystallization when printed layers are stored under normal conditions. The Table also shows the crystallinity reached during a DSC analysis as described above. Part A of the Table shows compounds derived from 2,2'-biphenol. The compounds in part B are derived from pentaerythritol, and the compounds in part C are similar compounds derived from dipentaerythritol. Compounds derived from 4,4'-dicyclohexylmethane diisocyanate are shown in part D. Finally, parts E and F show compounds derived from isophoron diisocyanate and diphenylmethane diisocyanate, respectively.

It is apparent from the Table that esters of 2,2'-biphenol with acids having an aromatic character are compounds defined by the present invention. They exhibit no demonstrable crystallinity under the conditions described above which means that in each case less than 1% of the compound is crystallized. On the other hand, the compound di-PET3T, for example, shows a crystallinity of 8%. In an ink composition this compound shows a just visible after-crystallization when a printed layer is stored for a number of weeks at room temperature and 50% relative air humidity.

TABLE 1

| Part | R | (abbreviation) | Disturbing after-crystallization | Crystallinity (%) |
|---|---|---|---|---|
| A | (2,2'-biphenyl diester: each ring —O—C(=O)—R) | | | |
| | para $CH_3O—C_6H_5—$ para-anisyl | (BIPANI) | no | <1 |
| | ortho $CH_3—C_6H_5—$ ortho-tolyl | (BIP2T) | no | <1 |
| | meta $CH_3—C_6H_5—$ meta-tolyl | (BIP3T) | no | <1 |
| | para $CH_3—C_6H_5—$ para-tolyl | (BIP4T) | no | <1 |
| | $C_6H_5O—$ phenoxy | (BIPPC) | no | <1 |
| B | $C—(CH_2—O—C(=O)—R)_4$ | | | |
| | $CH_3—$ methyl | (PETA) | yes | 100 |
| | $C_6H_5O—$ phenoxy | (PET-PC) | yes | 100 |
| C | $(R—C(=O)—O—CH_2)_3C—O—C(CH_2—O—C(=O)—R)_3$ | | | |
| | $CH_3—$ methyl | (di-PETA) | yes | 30 |
| | ortho $CH_3—C_6H_5—$ ortho-tolyl | (di-PET2T) | yes | 70 |
| | meta $CH_3—C_6H_5—$ meta-tolyl | (di-PET3T) | yes | 8 |
| | $C_6H_5—O—$ phenoxy | (di-PET-PC) | yes | 50 |
| D | RO—C(=O)—N(H)—(S)—$CH_2$—(S)—N(H)—C(=O)—OR | | | |
| | $C_6H_5—CH_2—$ phenyl(methyl) | (CMDI-BA) | yes | 68 |
| | $C_6H_5—CH_2—CH_2—$ phenyl(ethyl) | (CMDI-PEA) | yes | 15 |
| E | RO—C(=O)—N(H)—(S: ring with $H_3C$, $CH_2$—N(H)—C(=O)—OR, $CH_3$, $CH_3$) | | | |
| | iso $C_3H_7—$ iso-propyl | (IPDI-IPA) | yes | 12 |
| F | RO—C(=O)—N(H)—$C_6H_4$—$CH_2$—$C_6H_4$—N(H)—C(=O)—OR | | | |
| | $CH_3O—CH_2—CH_2—$ methyl(ethylether) | (MDI-MEG) | yes | 83 |

Table 1. Details of a selection of amorphously solidifying monomer compounds, with respect to the incidence of after-crystallization when transferred as part of an ink composition to a support and the crystallinity after cooling of a melt at 5° C./min and re-heating at 20° C./min.

Example 2

Crystallization in a Mixture with Crystalbond

After-crystallization of an amorphously solidifying monomer compound in a printed layer can be demonstrated more quickly by blending this compound with the oligomer binder Crystalbond 509 (compound: Crystalbond=2:1 weight/weight), placing the blend in an oven at 50° C. and assessing after 48 hours whether after-crystallization of the compound has occurred. This assessment can be carried out visually, since after-crystallization is combined with a fall-off in transparency of the blend. If required, the crystallization can be quantified by Differential Scanning Calorimetry.

Table 2 shows the properties of Crystalbond 509. Table 3 shows the results of this test for a number of monomer compounds. This also includes assessment of the stability of a printed layer when the binder used in the ink composition contains the compound in question. It is clear that the compounds which exhibit no after-crystallization in this test lead to the most stable printed layers in an ink composition.

TABLE 2

| Characteristics of the oligomer binder Crystalbond 509 of Printlas ™ | |
|---|---|
| Chemical structure | Polyethylene phthalate |
| Hydroxyl number (number of mg KOH/g) | 42 ± 10% |
| End group ratio | 58% hydroxyl, 42% carboxyl |
| $M_N$* | 1650 |
| $M_W$* | 4000 |
| Polydispersivity ($M_W M N_N$) | 2.4 |
| Tg | 28° C. ± 2° C. |

*Measured with respect to polystyrene standards

Table 2. Characteristics of Crystalbond 509

TABLE 3

| Compound | After-crystallization after 48 hours (visual assessment) | Printed layer stability |
|---|---|---|
| PET-PC | Considerable | Poor |
| di-PET2T | Considerable | Poor |
| CMDI-PEA | Considerable | Poor |
| di-PET3T | Considerable | Moderate |
| di-PET-PC | Considerable | Moderate |
| CMDI-BA | Considerable | Moderate |
| BIP2T | Moderate | Reasonable |
| BIP3T | Not present | Good |
| BIPPC | Not present | Good |
| BIP4T | Not present | Good |
| BIPANI | Not present | Very good |

Table 3. After-crystallization of a number of amorphously solidifying compounds from a blend with Crystalbond 509 (compound: Crystalbond=2:1 weight/weight) and an assessment of the stability of the printed layer when an ink composition contains the compound in a binder.

Example 3

Ink Compositions

Table 4 gives details of various ink formulations. The inks 1 to 4 are inks according to the invention. Layers printed with the inks 5 and 6 have a clear deterioration in quality within a number of weeks (particularly the transparency of the layers falls off due to after-crystallization of the low-molecular binder). The conventional additions can be made to each of the said inks, e.g. antioxidants, surface tension reducing compounds and colorants in the form of soluble dyes or pigments.

TABLE 4

| No. | Base material % by weight | Crystal-bond 509 % by weight | Low-molecular binder % by weight | Dye % by weight | Assess-ment |
|---|---|---|---|---|---|
| 1 | 68 p-BuBSA | 10 | 20 BIPANI | 2 Orasol Blau | Very good |
| 2 | 68 p-BuBSA | 0 | 30 BIPANI | 2 Orasol Blau | Good |
| 3 | 69.5 HQHE | 10 | 20 BIP4T | 0.5 Macrolex Rot | Good |
| 4 | 50 HQHE | 0 | 50 BIP4T | 0.5 Macrolex Rot | Good |
| 5 | 69.5 p-BuBSA | 10 | 20 di-PET2T | 0.5 Macrolex Rot | Poor |
| 6 | 69.5 HQHE | 10 | 20 CMDI-PEA | 0.5 Macrolex Rot | Poor |

Table 4. Ink compositions and an assessment of the stability of a printed layer. p-BuBSA=para-n-butyl benzene sulphonamide; HQHE=1,4 hydroquinone bis(2-hydroxyethyl) ether; CrystalBond 509=polyethylene phthalate resin of Printlas™.

Example 4

Synthesis of the Esters of 2,2'-biphenol and Aromatic Acids

The synthesis of the esters of 2,2'-biphenol and acids with an aromatic character is effected by reacting the alcohol with a small excess of the acid chloride. 12.5 g of 2,2'-biphenol were dissolved in 250 ml of pyridine in a round-bottom flask provided with a reflux cooler. 1,2 equivalents (with respect to the hydroxyl groups) of the acid chloride were then added drop-wise with constant agitation, this taking approximately one-half hour. The mixture may boil in these conditions. After all the acid chloride has been added, the mixture was agitated for 3 hours and slowly cooled to room temperature. The mixture was then poured into a saturated $NaHCO_3$ solution (about 300 ml). The mixture was then washed with 3×250 ml $CH_2Cl_2$, after which all the product was taken up in the $CH_2Cl_2$. The $CH_2Cl_2$ was decanted, washed a number of times with water and finally dried with $Na_2SO_4$. The solution was filtered off and dried in vacuo. If required the compounds can be recrystallized in ethanol to obtain a higher degree of purity. The resulting BIPANI had a melting point of 125° C., BIP4T had a melting point of 117° C.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An ink composition for a meltable ink usable in a printing apparatus which comprises an ink containing an amorphously solidifying monomer compound, having a crystallinity of less than 1% when a melt of the compound is cooled at a rate of 5° C./min to past its solidification point and is then heated at a rate of 20° C./min to above its melting temperature.

2. The ink composition according to claim 1, wherein the amorphously solidifying compound exhibits a crystallinity of less than 1% when a melt of the compound is cooled at a rate of 5° C./min to past its solidification point and is then heated at a rate of 5° C./min to above its melting temperature.

3. The ink composition according to claim 1, wherein the amorphously solidifying compound, when blended with polyethylene phthalate in a ratio of 2:1 (weight/weight), remains amorphous at 50° C. for at least 48 hours.

4. The ink composition according to claim 1, wherein the amorphously solidifying compound is selected from the group having the molecular formula:

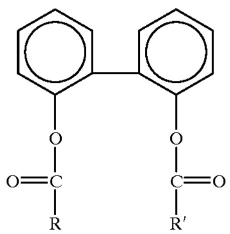

where R and R' have an aromatic character.

5. The ink composition according to claim 4, wherein R and R' are selected from the group consisting of

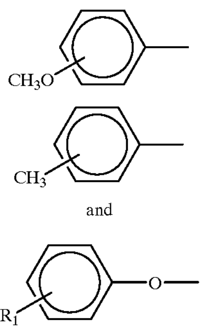

wherein R1 can be at least one C1–C4 alkyl group or H.

6. The ink composition according to claim 5, wherein R and R' are selected from the group consisting of para-anisyl, para-tolyl and phenoxy.

7. The ink composition according to claim 6, wherein R and R' are identical.

8. An ink composition for a meltable ink, which comprises an ink containing a meltable base material, an amorphously solidifying monomer compound having a crystallinity of less than 1% when a melt of the compound is cooled at a rate of 5° C./min to past its solidification path and is then heated at a rate of 20° C./min to above its melting temperature, and an amorphous polymer or oligomer binder, said base material being a crystalline-solidifying monomer compound.

9. The ink composition according to claim 8, wherein the amorphously solidifying monomer compound shows a crystallinity of less than 1% when a melt of the compound is cooled at a rate of 5° C./min to past its solidification path and is then heated at a rate of 5° C./min to above its melting temperature.

10. The ink composition according to claim 9, wherein when the amorphously solidifying compound is blended with polyethylene phthalate in a ratio of 2:1 (weight/weight), it remains amorphous at 50° C. for at least 48 hours.

11. The ink composition of claim 8, wherein the amorphously solidified monomer compound is selected from the group having the molecular formula:

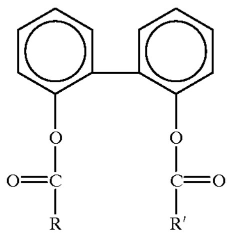

where R and R' have an aromatic character.

12. The ink composition according to claim 11, wherein R and R' are selected from the group consisting of

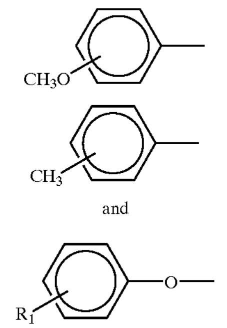

wherein R1 can be at least one C1–C4 alkyl group or H.

13. The ink composition according to claim 12, wherein R and R' are selected from the group consisting of para-anisyl, para-tolyl or phenoxy.

14. The ink composition according to claim 13, wherein R and R' are identical.

* * * * *